US00PP32088P3

(12) United States Plant Patent
Scattini

(10) Patent No.: US PP32,088 P3
(45) Date of Patent: Aug. 18, 2020

(54) ARTICHOKE PLANT NAMED 'PAGA 15-1'

(50) Latin Name: ***Cynara cardunculus* L. var. *scolymus***
Varietal Denomination: PAGA 15-1

(71) Applicant: Michael R. Scattini, Salinas, CA (US)

(72) Inventor: Michael R. Scattini, Salinas, CA (US)

(73) Assignee: LUIS A. SCATTINI & SONS, LP, Salinas, CA (US)

( * ) Notice: Subject to any disclaimer, the term of this patent is extended or adjusted under 35 U.S.C. 154(b) by 0 days.

(21) Appl. No.: 16/501,352

(22) Filed: Mar. 29, 2019

(65) Prior Publication Data

US 2019/0307039 P1 Oct. 3, 2019

Related U.S. Application Data

(60) Provisional application No. 62/650,945, filed on Mar. 30, 2018.

(51) Int. Cl.
*A01H 5/00* (2018.01)
*A01H 6/14* (2018.01)

(52) U.S. Cl.
USPC ..... Plt./258
CPC ..... *A01H 6/14* (2018.05); *A01H 6/1432* (2018.05)

(58) Field of Classification Search
USPC ..... Plt./258
CPC ..... A01H 6/1432; A01H 6/14; A01H 5/00
See application file for complete search history.

(56) References Cited

U.S. PATENT DOCUMENTS

| | | | |
|---|---|---|---|
| 1,758,128 | A | 5/1930 | Rosevear |
| 2,069,958 | A | 2/1937 | Diemer |
| 2,663,137 | A | 12/1953 | Asbury |
| 2,775,065 | A | 12/1956 | Chepil et al. |
| 3,645,041 | A | 2/1972 | Addin |
| 4,023,506 | A | 5/1977 | Robey |
| 5,060,418 | A | 10/1991 | Pullman et al. |
| 9,596,825 | B1 | 3/2017 | Peng |
| 2006/0242899 | A1 | 11/2006 | Parmenter |
| 2008/0155890 | A1 | 7/2008 | Oyler |
| 2010/0083569 | A1 | 4/2010 | Danalatos et al. |
| 2012/0227122 | A1 | 9/2012 | Arrieta |
| 2013/0005569 | A1 | 1/2013 | Hendickson et al. |
| 2015/0373927 | A1 | 12/2015 | Paans |
| 2016/0242368 | A1 | 8/2016 | Levine |
| 2016/0255778 | A1 | 9/2016 | Redden et al. |
| 2017/0215353 | A1 | 8/2017 | Schurter et al. |
| 2017/0359961 | A1 | 12/2017 | Scattini |
| 2019/0297818 | A1 | 10/2019 | Scattini |
| 2019/0307040 | P1 | 10/2019 | Scattini |
| 2019/0307041 | P1 | 10/2019 | Scattini |

FOREIGN PATENT DOCUMENTS

| | | | |
|---|---|---|---|
| CA | 2976783 | A1 | 8/2016 |
| FR | 3012797 | B1 | 12/2015 |

OTHER PUBLICATIONS

Acar et al., (2011). "Effects of different mowing dates of plant top on tuber yield of Jerusalem artichoke (*Helianthus tuberosus* L.)," African Journal of Biotechnology Col, 10(45):9036-9040.
Bedini et al., (2012). "Plant tissue cultures from four Tuscan globe artichoke cultivars," Open Life Sciences, 7(4):680-689.
Boullani et al., (2012). "Improved in Vitro Micropropagation of Artichoke {*Cynara cardunculus* Var. *scolymus* L)," European Journal of Scientific Research, 80(4):430-436.
Bratsch et al., (2009). "Specialty Crop Profile: Globe Artichoke," Virginia Cooperative Extension Publication, 438-108. <http://pubs.ext.vt.edu/438/438-108/438-108_pdf.pdf.>.
Ceccarelli et al., (2010). "Globe Artichoke as a Functional Food," Mediterranean Journal of Nutrition and Metabolism, 3:197-201.
Iapichino (2013). "Micropropagation of Globe Artichoke (*Cynara Cardunculus* L. Var. *scolymus*)," Methods in Molecular Biology, 994:369-380.
Iapichino (1996). "Micropropagation of Globe Artichoke (*Cynara scolymus* L.) from Underground Dormant Buds ("'Ovoli")," In Vitro Cellular & Developmental Biology. Plant, 32:249-252.
Murashige (1974). "Plant Propagation through Tissue Cultures," Annual review of plant physiology, 25:135-166.

*Primary Examiner* — Keith O. Robinson
(74) *Attorney, Agent, or Firm* — Morrison & Foerster LLP

(57) ABSTRACT

A new and distinct variety of artichoke (*Cynara cardunculus* var. *scolymus* L.) plant named 'PAGA 15-1', particularly characterized by its high yield, large primary bud size, large number of secondary and tertiary buds, wide bracts with fleshy base, thick stems, and early maturity, is disclosed.

10 Drawing Sheets

Latin name:

Botanical classification: *Cynara cardunculus* L. var. *scolymus.*

Varietal denomination: Varietal denomination of the claimed artichoke variety: 'PAGA 15-1'.

BACKGROUND OF THE INVENTION

Artichoke (*Cynara cardunculus* L. var. *scolymus*), or globe artichoke, is a thistle-like perennial plant native to the Mediterranean region and is a member of the family Asteraceae. Artichoke belongs to the species *Cynara cardunculus* L. that includes two subspecies/cultivation groups: the cardoon (*Cynara cardunculus* L. var. *altilis*) that is cultivated for its edible leaf stems, and the artichoke that is cultivated for its edible immature inflorescence hereinafter referred to as buds, heads, or capitula. In some instances, artichoke is distinguished as *Cynara scolymus.*

Artichoke is a popular vegetable food source in many regions of the world, with nearly two million tons of artichokes produced annually. The United States produces approximately 40,000 tons of artichokes annually, with California being responsible for nearly 100% of its production, of which about 80% is grown in Monterey County.

Historically, a common perennial artichoke variety that is grown in the United States is 'Green Globe', also referred to as an "Heirloom" artichoke. Despite the use of it as a traditional cultivar, 'Green Globe' does not produce large numbers of large buds which are most desired by consumers. Further, 'Green Globe' exhibits a substantial amount of phenotypic variation as well as protracted and unpredictable harvest intervals.

Thus, there exists a need for improved artichoke varieties having large sized post-primary bud production, programmable and predictable harvest timing, and better uniformity. The present artichoke variety described herein is a product of the efforts to develop such artichoke varieties.

BRIEF SUMMARY

The present disclosure relates to a new and distinct artichoke variety (*Cynara cardunculus* L. var. *scolymus*) which has been denominated as 'PAGA 15-1'. This new artichoke variety exhibits increased bud yield, size and plant vigor compared to 'Green Globe', and produces a large primary bud, about 6-13 secondary buds, and about 6-11 tertiary buds per primary reproductive shoot. Up to 8 of the primary and secondary buds are 12-15 inches in circumference. Between 3-4 of the secondary and tertiary buds are 10¾-12½ inches in circumference or larger. The remaining buds are generally between 3-10½ inches in circumference. The plants produce between 1 and 6 reproductive shoots, in addition to the primary reproductive shoot, in the first production cycle. These secondary reproductive shoots produce less marketable sized buds than the primary shoot, although cultural practices such as cutting the primary reproductive shoot from the plant after harvest can materially increase the size and number of buds produced by these secondary shoots.

The new artichoke variety described herein is the product of an artichoke plant improvement program conducted over a number of years. The original parent is the unpatented *Cynara cardunculus* L. var. *scolymus* variety 'Green Globe', commonly known and cultivated in Castroville, Calif. for more than 90 years. This improvement project began with the objective to develop an artichoke variety with superior bud production. This included selecting for improvements in both commercial quality of buds, as well as overall bud consistency and large size bud production per plant. Additionally, plants were selected based on their predictable and condensed harvest phase.

The new artichoke variety described herein was discovered after several years of isolating and propagating artichoke variety 'Green Globe' in Castroville, Calif. From this continual propagation, several selections were identified which exhibited superior yield characteristics as compared to 'Green Globe'. During this process, no crosses were made between 'Green Globe' and another artichoke variety, and these identified selections with superior yield characteristics were presumably results of natural mutations of 'Green Globe'. After identifying the superior quality plants from field conditions, the highest quality plants were selected for induction into laboratory tissue culture reproduction. These tissue-cultured plants were then planted in a test field in Castroville, Calif., where further selections were made among the population. Selections from this field were propagated by tissue culture, with subsequent field selections and tissue culture propagation conducted. The variety described herein as 'PAGA 15-1' is a final product obtained from these selections and tissue culture propagation cycles.

Artichoke plant 'PAGA 15-1' was subsequently asexually reproduced via tissue culture propagation and regeneration of artichoke plants from plantlets. The present variety has been found to be stable and reproduce true to type through successive asexual propagations.

'PAGA 15-1' exhibits the following distinguishing characteristics when grown under normal horticultural practices in Castroville, Calif.:

1. Large bud size;
2. Primary reproductive shoots produce at least 6 secondary buds, and at least 6 tertiary buds; on average, the number of lateral heads on the main stem of the plant ranges from 12 to 24;
3. Plants produce an average of 4 reproductive shoots, in addition to the primary reproductive shoot, during the first production cycle;
4. Bracts and receptacles are wide, and thick;
5. Large diameter peduncle; and
6. Early maturity.

DESCRIPTION OF THE DRAWINGS

The accompanying photographs illustrate the overall appearance of the new artichoke plant 'PAGA 15-1' showing the colors as true as is reasonably possible with colored reproductions of this type. Colors in the photographs may differ slightly from the color values cited in the detailed botanical description, which accurately describes the color of this variety. The depicted plant and plant parts of the new artichoke plant 'PAGA 15-1' are from plants that are 5-6 months old, grown in Castroville, Calif.

DETAILED BOTANICAL DESCRIPTION

Figure 1:
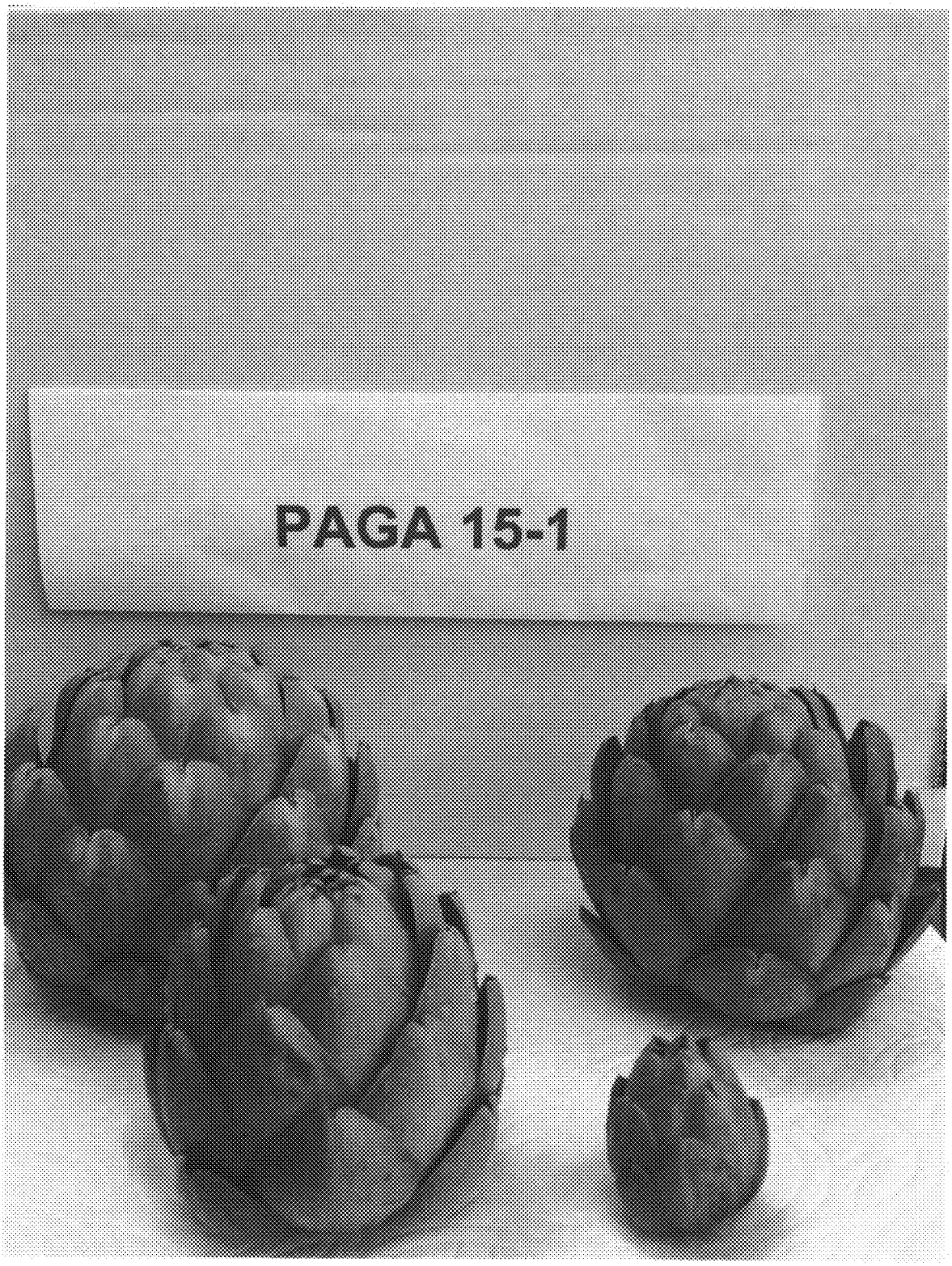
FIG. 1 shows various sized capitula (buds) of 'PAGA 15-1'.
Figure 2:
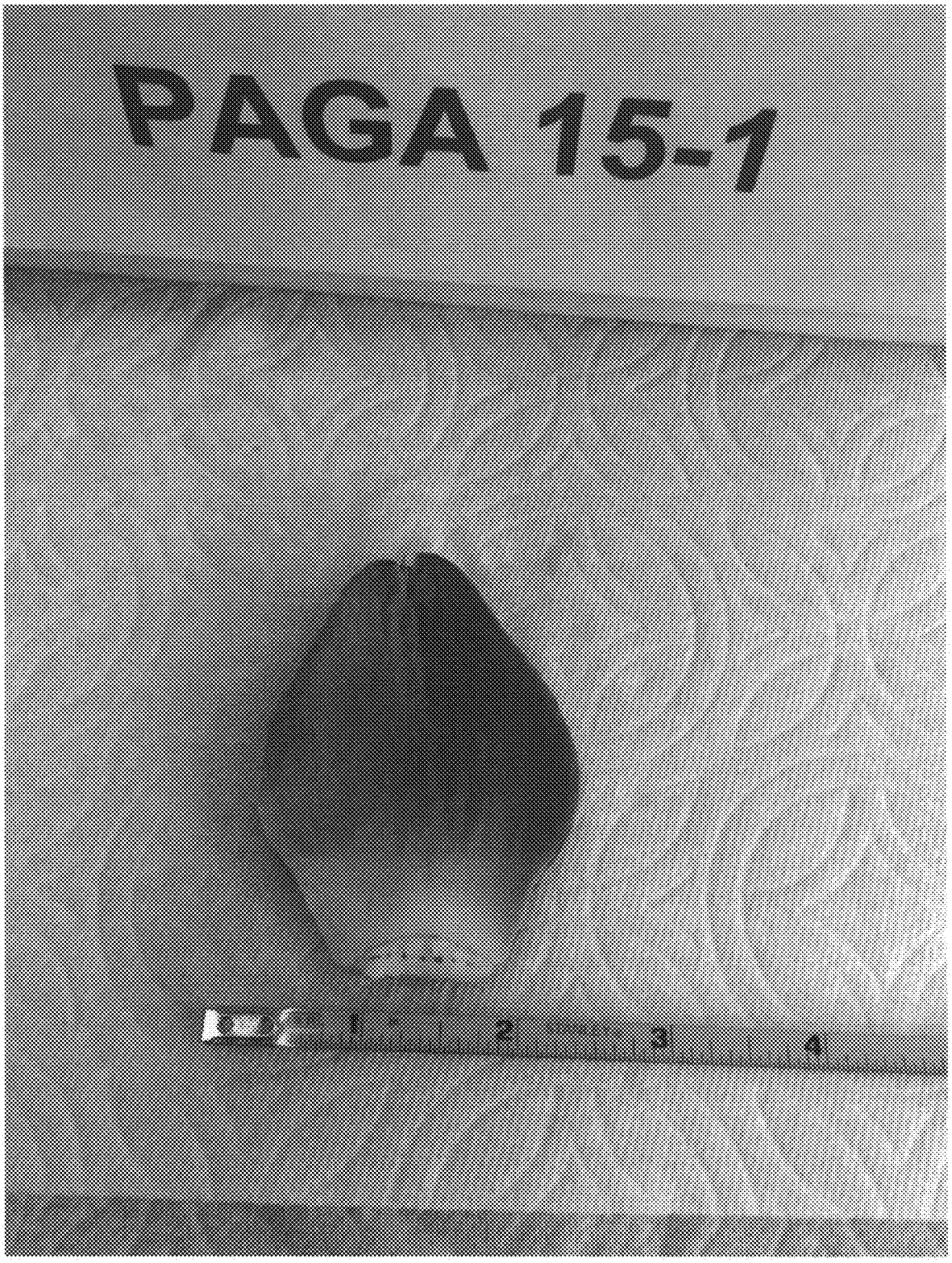
FIG. 2 shows an interior view of a bract of 'PAGA 15-1'.
Figure 3:
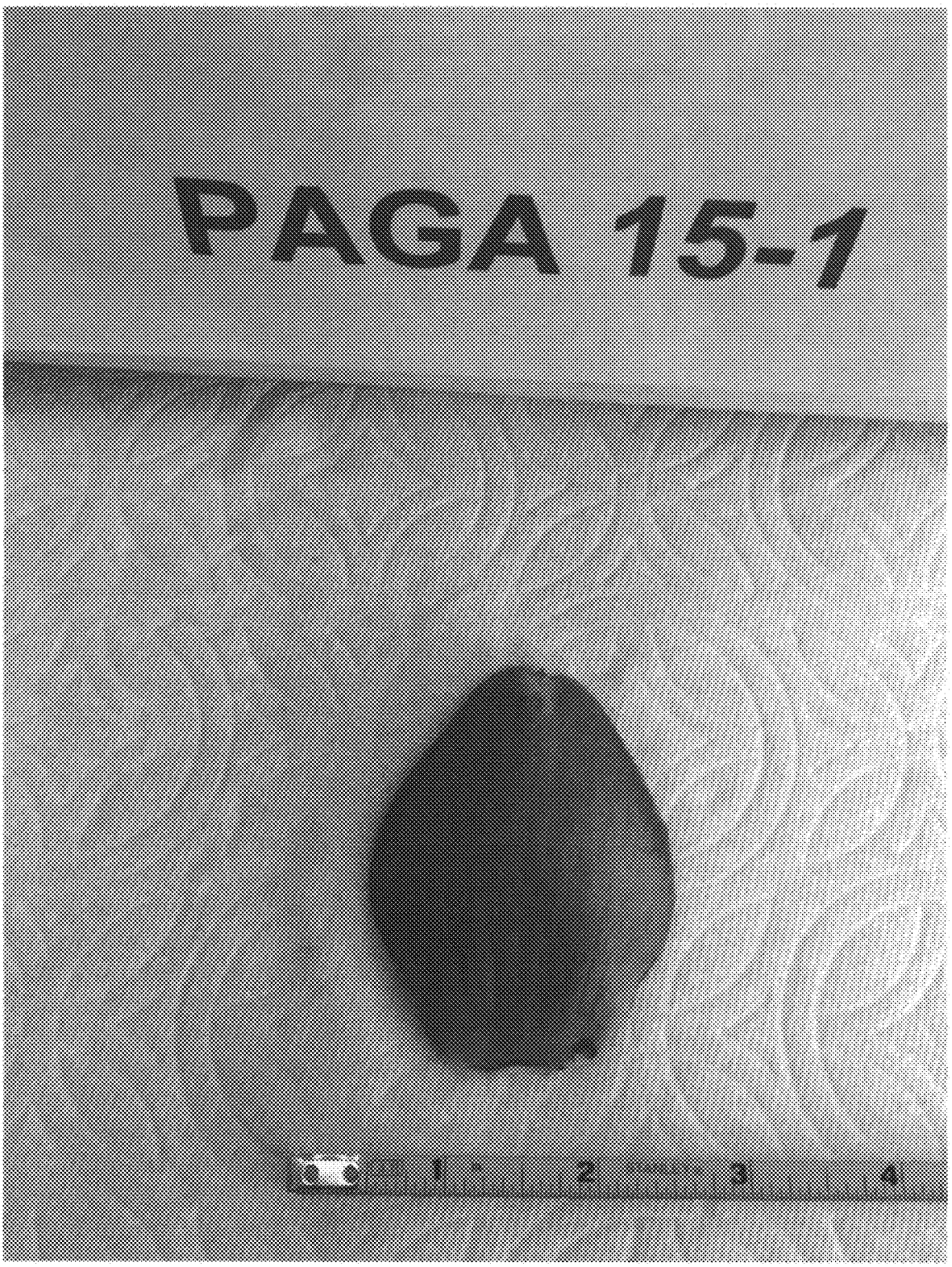
FIG. 3 shows an exterior view of a bract of 'PAGA 15-1'.
Figure 4:
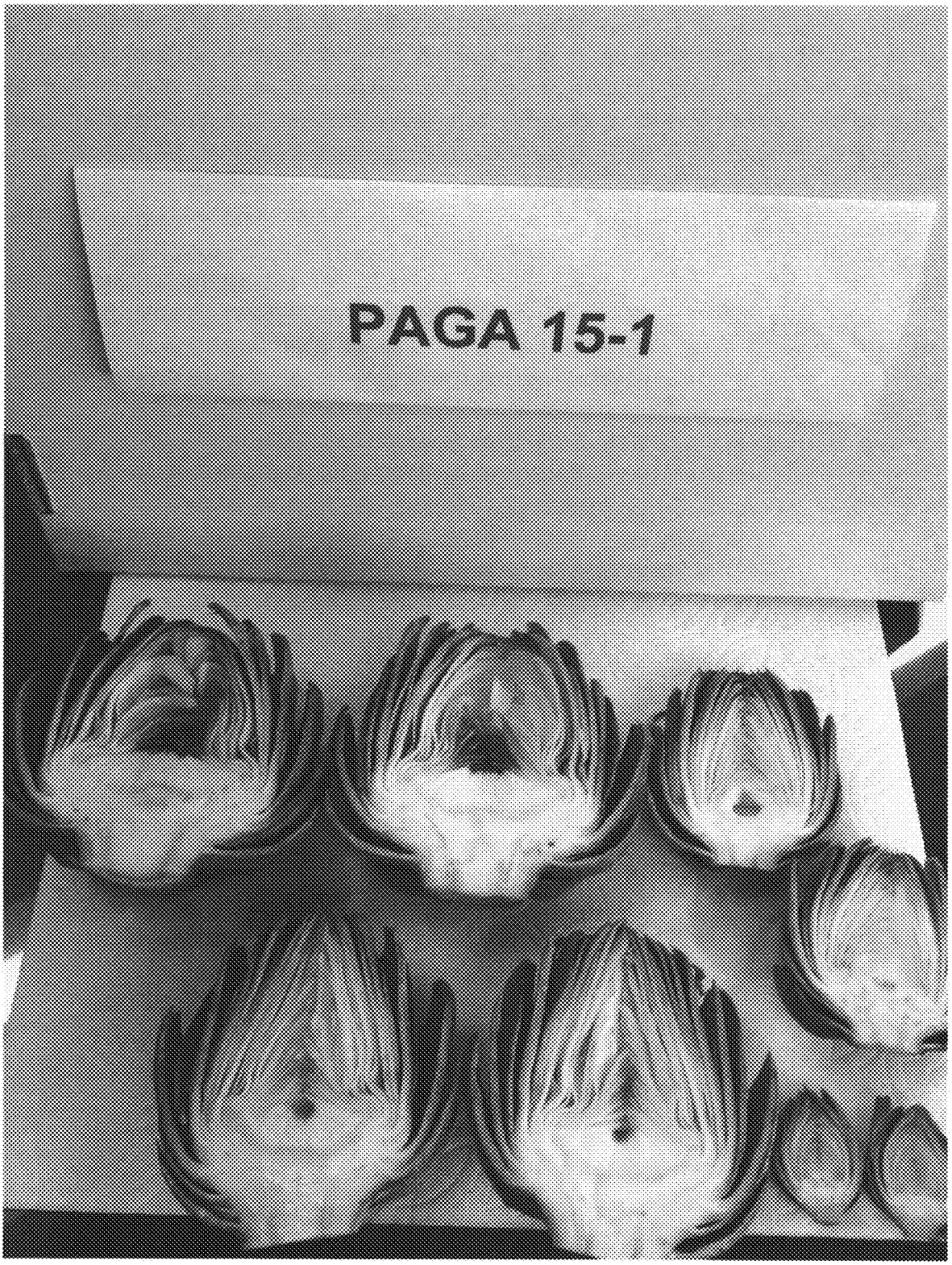
FIG. 4 shows a cross section view of various sized capitula (buds) of 'PAGA 15-1'.
Figure 5:
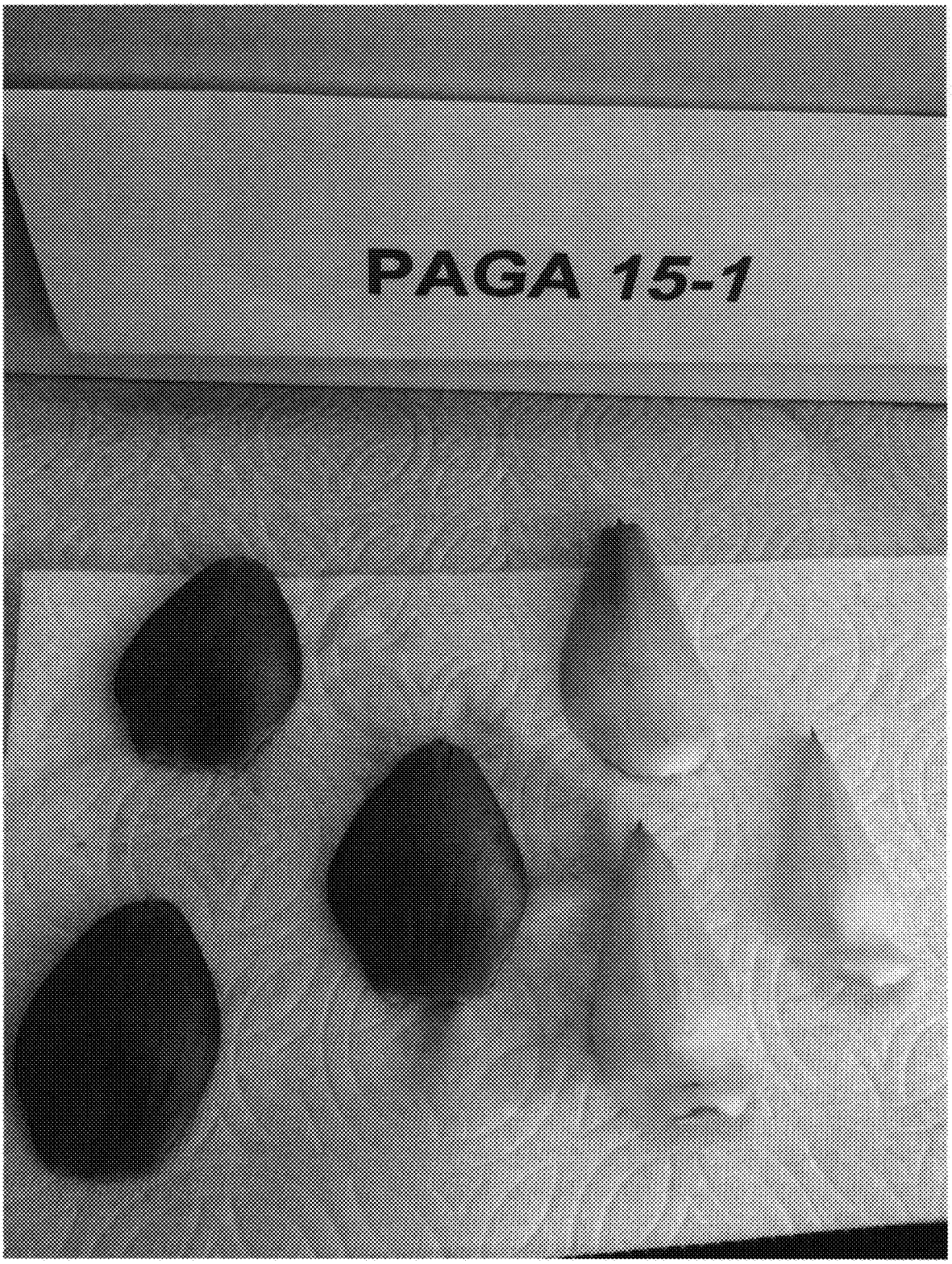
FIG. 5 shows examples of outer and inner bracts of 'PAGA 15-1'.
Figure 6:
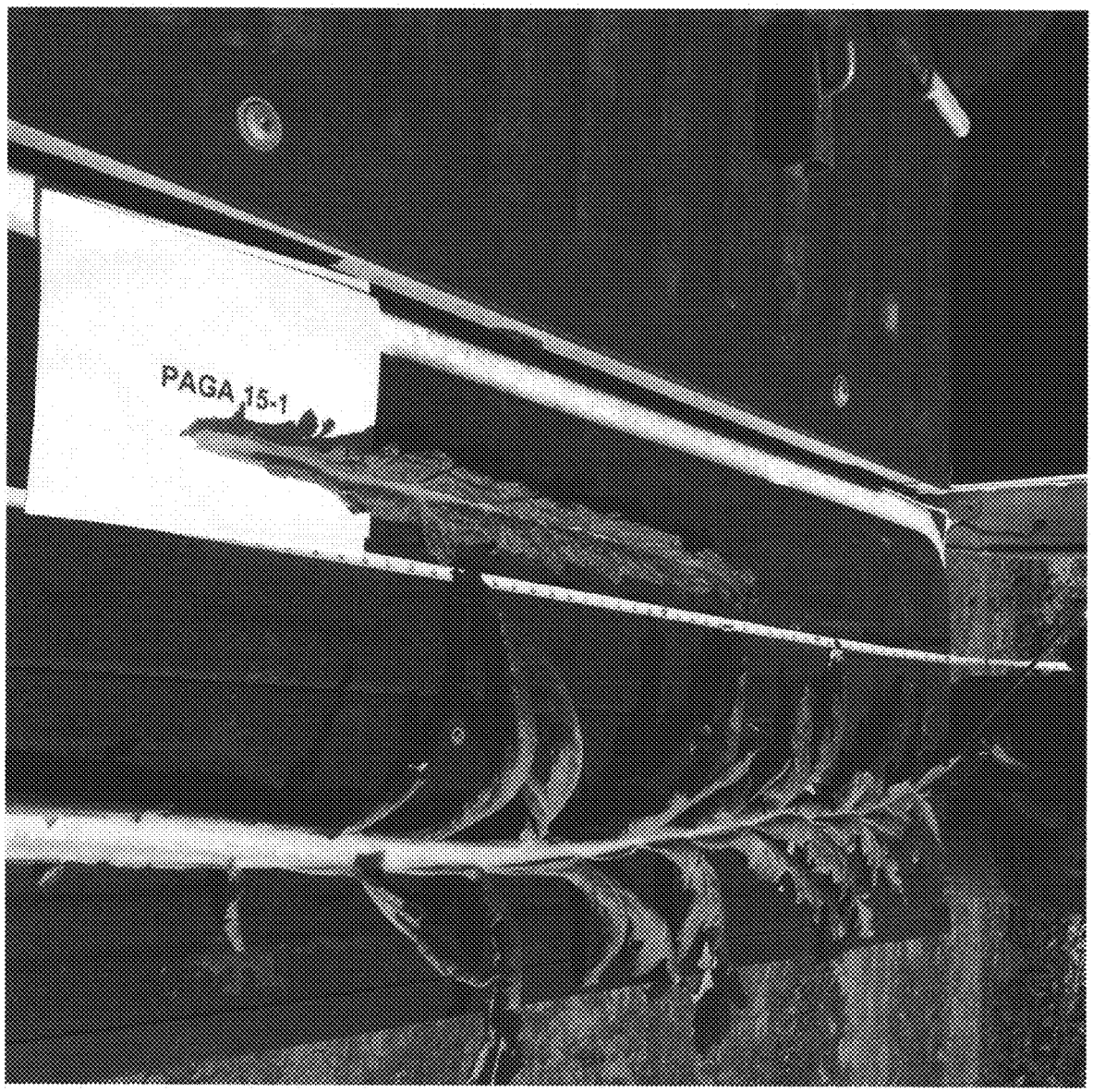
FIG. 6 shows a cauline and a basal rosette leaf of 'PAGA 15-1'.
Figure 7:
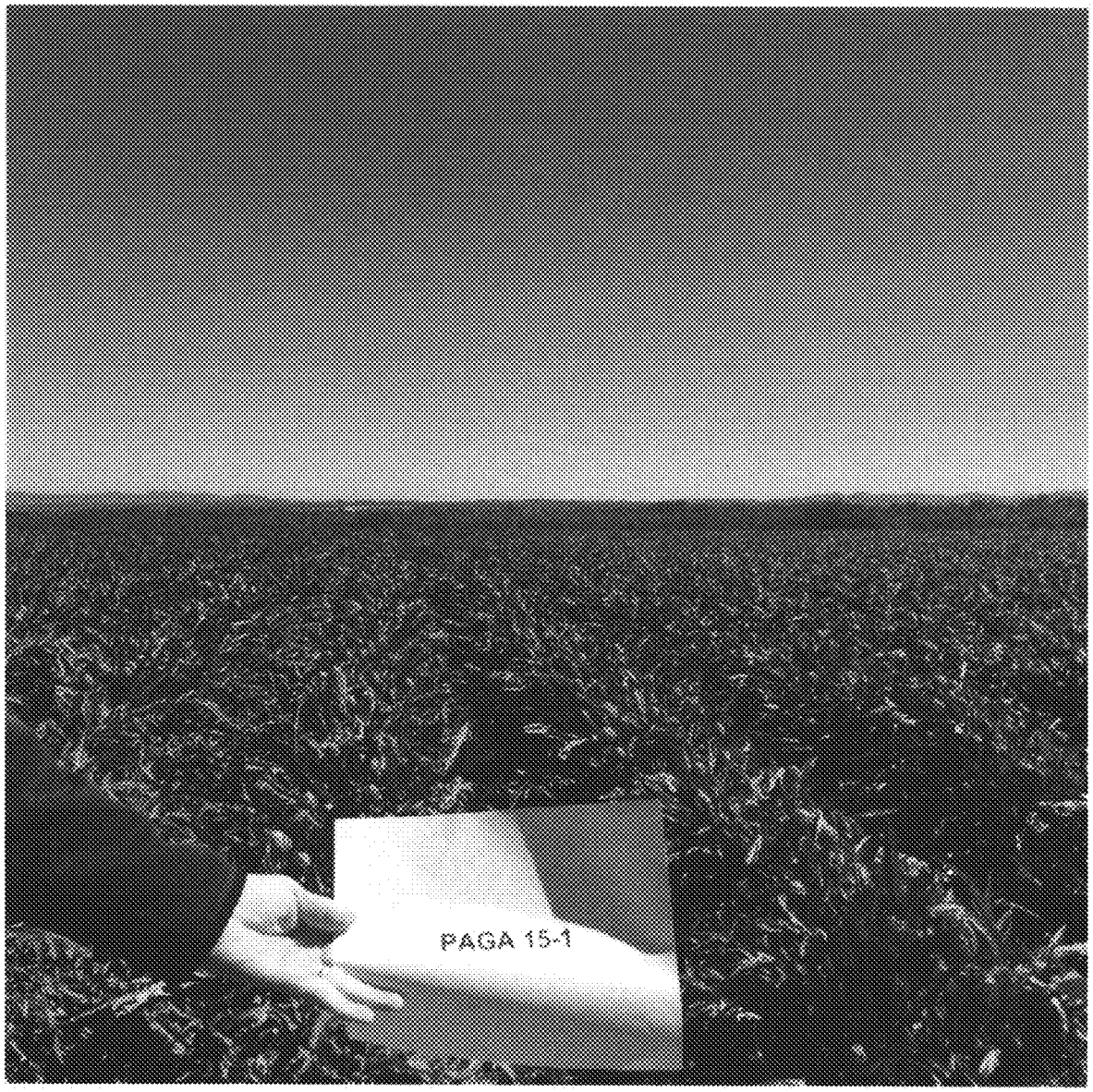
FIG. 7 shows a growing field of 'PAGA 15-1' demonstrating its uniformity.
Figure 8:
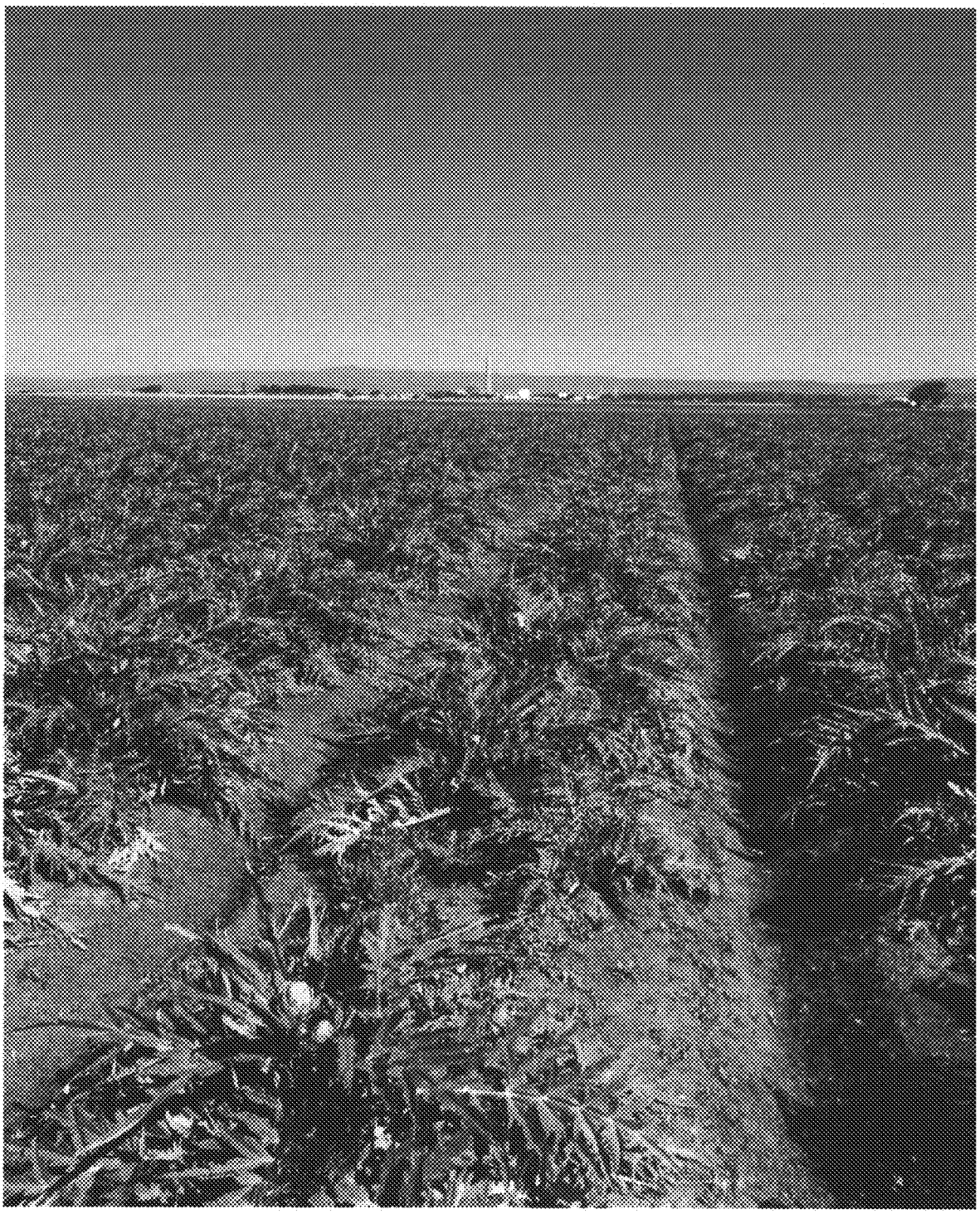
FIG. 8 shows a growing field of the parent variety 'Green Globe' demonstrating its lack of uniformity.
Figure 9:
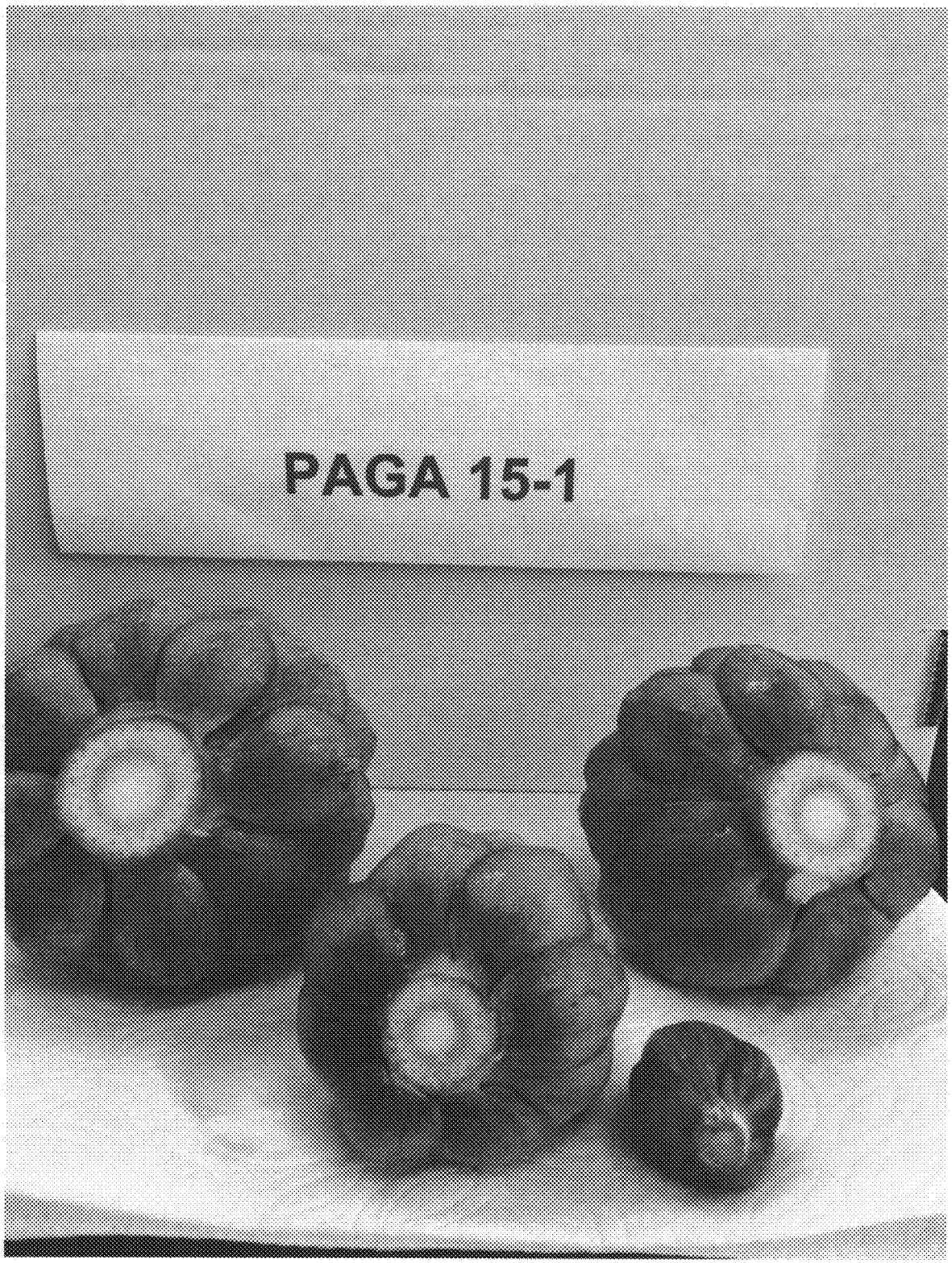
FIG. 9 shows various sized 'PAGA 15-1' capitulum (bud) bases showing the differences in purple colored striations on lower bracts.
Figure 10:
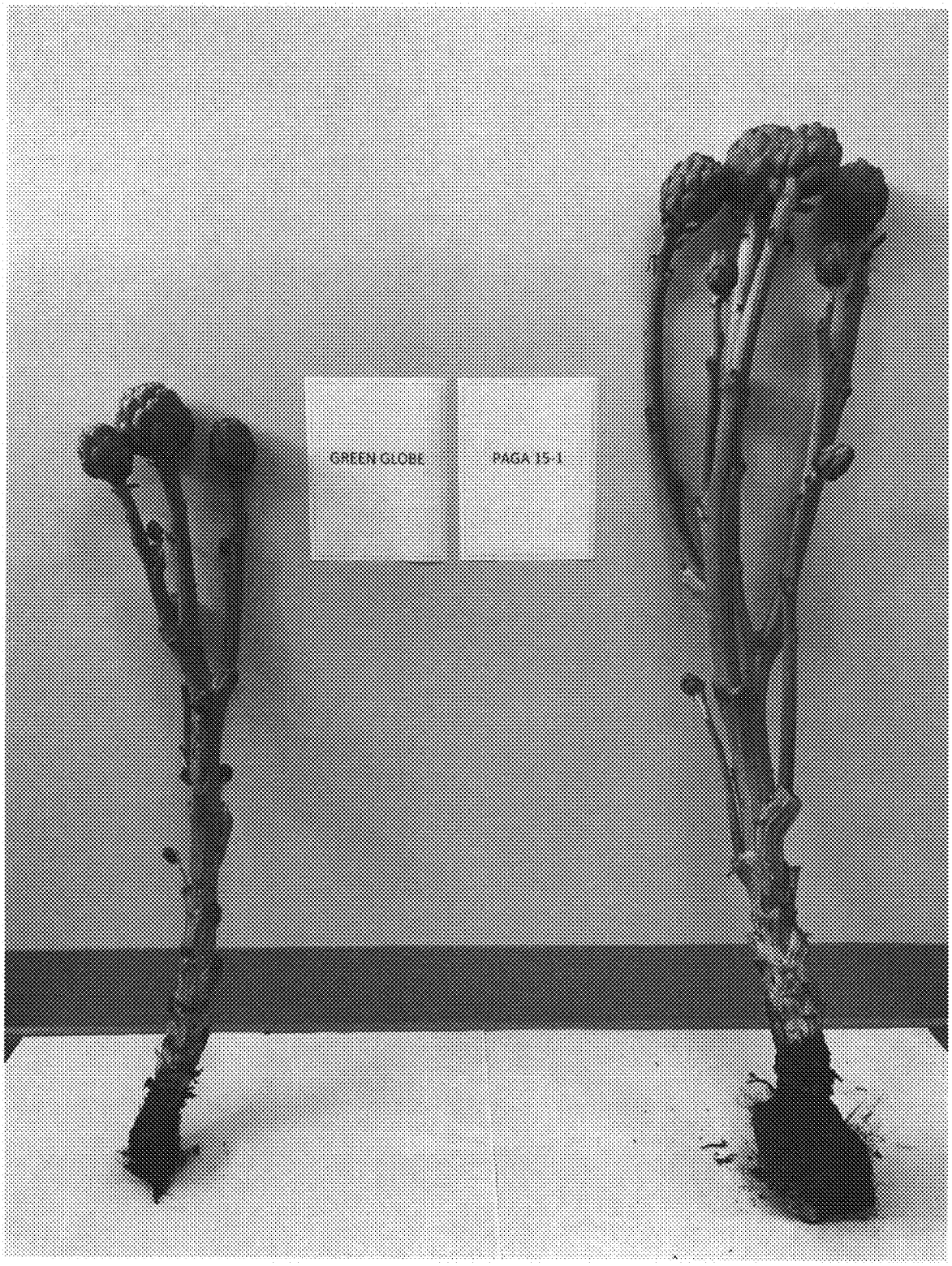
FIG. 10 shows 'PAGA 15-1' (right) and 'Green Globe' (left) reproductive stems that have been stripped of leaves.

The following detailed descriptions set forth the distinctive characteristics of 'PAGA 15-1'. The data which define these characteristics is based on observations taken in Castroville, Calif. This description is in accordance with UPOV terminology. Color designations, color descriptions, and other phenotypical descriptions may deviate from the stated values and descriptions depending upon variation in environmental, seasonal, climatic, and cultural conditions.

'PAGA 15-1' has not been observed under all possible environmental conditions. The botanical description of 'PAGA 15-1' was taken from plants that were 5-6 months old. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2nd edition by James G. Harris and Melinda Woolf Harris, unless where otherwise defined.

Classification:

*Taxonomic name.*—*Cynara cardunculus* L. var. *scolymus.*

*Common name.*—Globe Artichoke.

*Denomination.*—'PAGA 15-1'.

Parentage: *Cynara cardunculus* var. *scolymus* L. 'PAGA 15-1' was discovered through successive plant selections, and tissue culture propagation cycles of *Cynara cardunculus* L. var. *scolymus* variety 'Green Globe'.

TABLE 1

| Plant Characteristics | |
|---|---|
| | PAGA 15-1 |
| General information | |
| Propagation Method: | Tissue culture |
| Months of harvest: | Year round with greatest productivity February through June |
| Number of days from planting to first harvest | Range: 165-203 Average: 190 (tissue culture) |
| Duration of harvest cycle: | Average: 72 days |
| Plant | |
| Height range at harvest (vegetative): | 167.64-177.8 cm (66-74 inches) |
| Height average at harvest (vegetative): | 182.88 cm (72 inches) |
| Width at harvest (vegetative): | 152.4-284.48 cm (60-112 inches) |
| Growth Habit: | Upright, with horizontal spread of older leaves and shoots |
| Form: | Arch |
| Vigor: | Very Good |
| Root system: | Thick and fibrous |
| Foliage Density: | Dense, increasing as secondary reproductive shoots develop |
| Male sterility: | Absent |
| Primary Reproductive Shoot | |
| Height to primary (terminal) bud top: | 152.4 cm-193.04 (60-76 inches) |
| Number of leaves (rosette) | 25-32 (average 29) |
| Secondary Reproductive Shoots | |
| Number per plant in first production cycle: | 1-6 (average 4) |
| Height to primary (terminal) bud top: | 40.64-121.92 cm (16-48 inches) |
| Number of leaves | 7-25 (average 17) |
| Foliage | |
| Venation: | Reticulate |
| Leaf ratio (L/W): | Approximately 1.1-3.23 |
| Upper leaf surface color: | RHS 143A-143B (Green Group) |
| Lower leaf surface color: | RHS 141D (Green Group) |
| Leaf texture: | Glabrous and slightly glossy appearance in cool, damp conditions with interveinal texture. |
| Pubescence: | Slightly tomentose on upper surface, moderately tomentose on lower. More visible in dry/warm conditions. |
| Petiole color: | RHS 142B-142C (Green Group) |
| Petiole and mid rib texture: | Furrowed on upper side with lower side deeply ribbed with ridges running parallel to the lengthwise orientation. Sparsely arachnoid. |
| 1. Basal rosette leaves | |
| Shape: | Deeply pinnatifid (i.e. strong lobing) with sparsely ciliate margins, narrowly trullate overall. Narrowly acuminate apex is less acute than Green Globe. |
| Size: | Very large, >198.12-72.55 cm (78 × 32.5 inches) |
| Distance between leaf division: | 6.35-12.7 cm (2½-5 inches) |
| Division indentation length: | 16.51-41.275 cm (6½-16¼ inches) |
| Petiole length: | 30.48-57.15 cm (12-22½ inches) |
| Petiole width: | 3.175-9.525 cm (1¼-3¾ inches) |
| Petiole thickness: | 0.635-1.905 cm (¼-¾ inches) |
| Midrib thickness: | Thick |
| 2. Cauline leaves | |
| Shape: | Ensiform overall, uneven and sparse serrations with narrowly acuminate apex. Somewhat undulate and dented and sparsely ciliate at margins, |
| Number of leaves: | Approximately 100 |
| Size: | 17.78-60.96 cm (7-24 inches) |
| Stem (primary reproductive stem system) | |
| Length (ground level to base of terminal capitulum (bud)): | 152.4 cm-193.04 (60-76 inches) |
| Circumference: (base of terminal capitulum (bud): | 7.62-13.97 cm (3-5½ inches) |
| Circumference (base of stem): | Average: 35.56 cm (14 inches) |
| Exterior texture: | Vertically ribbed, pubescent |
| Stem habit: | Upright, caulescent |
| Pubescence: | Sparsely arachnoid |
| Color: | RHS 142A-142B |
| Time of beginning of elongation: | Early |
| Involucre bracts | |
| Arrangement: | Imbricate |
| Quantity per Capitulum (average): | 52 outer - 35 inner |
| Outer bract | |
| Shape: | Predominately ovate with flattened base |
| Apex: | Retuse |
| Margin: | Entire |
| Base: | Slightly rounded, thick |
| Texture: | Firm, thick and fleshy |
| Color: | RHS 142A-142B (Green Group) |
| Surface (outer/inner): | Glabrous |
| Spinosity: | Frequent, woody |
| Length of spines: | 1-5 mm (0.04-0.2 inches) |
| Striation at base of lower bracts: | Very minor - only present on the margins of a few lower outside bracts. More apparent on immature buds. |
| Striation color: | RHS 77A (Purple-Violet Group) |
| Inner bract | |
| Shape: | Lanceolate with caudate tip |
| Apex: | Retuse |
| Margin: | Entire |

TABLE 1-continued

| Plant Characteristics | |
|---|---|
| Texture: | Firm, thinner than outer bract, fleshy |
| Base: | Slightly rounded |
| Color: | RHS 150B-150C (Green Group) |
| Surface (outer/inner): | Glabrous |
| Spinosity: | Finer than outer bract, more frequent |
| Length of spines: | 1-2 mm (0.04-0.079 inches) |
| Capitulum (head/bud) - when ready for harvest as edible bud | |
| Color: | RHS 142A-142B (Green Group) |
| Shape: | Globose to ovoid |
| Apex: | Broadly rounded to obtuse |
| Base: | Truncate to rounded |
| Form: | Tightly compact |
| Texture: | Firm |
| Receptacle shape: | Concavo-convex |
| 1. Primary (Terminal) Capitulum | |
| Number per primary shoot | 1 |
| Circumference: | 34.925-43.18 cm (13¾-17 inches) |
| Weight: | Average 470 grams (1.03 lbs) |
| Height: | Average 10.795 cm (4¼ inches) |
| Diameter: | 12.7-15.24 cm (5-6 inches) |
| 2. Secondary capitulum | |
| Number per primary shoot | 6-13 |
| Circumference | 7.62-33.02 cm (3-13 inches) |
| Weight: | Average 199.3 grams (0.4394 lbs.) |
| Height: | Average 8.255 cm (3¼ inches) |
| Diameter: | 2.54-10.795 cm (1-4¼ inches) |
| 3. Tertiary capitulum | |
| Number per primary shoot | 6-11 |
| Circumference | 7.62-15.875 cm (3-6¼ inches) |
| Weight: | Average 36 grams (0.07936 lbs.) |
| Height: | Average 7.62 cm (3 inches) |
| Diameter: | 5.08-8.255 cm (2-3¼ inches) |
| Receptacle (heart) - when ready for harvest and edible | |
| Shape: | Concavo-convex |
| Circumference: | 8.89-25.4 cm (3½-10 inches) |
| Color: | RHS 150D (Green Group) |
| Texture: | Firm |
| Size: | Very thick and wide when compared to other globe varieties |
| Peduncle | |
| Shape: | Columnar |
| Length: | 2.54-101.6 cm (1-40 inches) |
| Diameter: | .635-4.445 cm (¼-1¾ inches) |
| Color: | RHS 142A-142B (Green Group) |
| Strength: | Strong and rigid |
| Surface: | Glabrous, slightly pubescent with shallow vertical ribbing |

| Green Globe | |
|---|---|
| General information | |
| Propagation Method: | Crown division |
| Months of harvest: | Year round with greatest productivity February through June |
| Number of days from planting to first harvest | Range: 161-212 Average 195 (crown division) |
| Duration of harvest cycle: | Average: 232 days |
| Plant | |
| Height range at harvest (vegetative): | 119.38-167.64 cm (47-66 inches) |

TABLE 1-continued

| Plant Characteristics | |
|---|---|
| Height average at harvest (vegetative): | 147.32 cm (58 inches) |
| Width at harvest (vegetative): | 114.3-132.08 cm (45-52 inches) |
| Growth Habit: | Upright, with horizontal spread of older leaves and shoots |
| Form: | Arch |
| Vigor: | Moderate |
| Root system: | Thick and fibrous |
| Foliage Density: | Moderately dense. |
| Male sterility: | Absent |
| Primary Reproductive Shoot | |
| Height to primary (terminal) bud top: | 106.68-137.16 cm (42-54 inches) |
| Number of leaves (rosette) | 14-28 (average 20) |
| Secondary Reproductive Shoots | |
| Number per plant in first production cycle: | 1-2 (average 1) |
| Height to primary (terminal) bud top: | 13.97-76.2 cm (5.5 to 30 inches) |
| Number of leaves | 3-16 (average 7.5) |
| Foliage | |
| Venation: | Reticulate |
| Leaf ratio (L/W): | Approximately 1.12-2.28 |
| Upper leaf surface color: | RHS 141A-141B (Green Group) |
| Lower leaf surface color: | RHS 136D (Green Group) |
| Leaf texture: | Glabrous and slightly glossy appearance in cool, damp conditions with interveinal texture. |
| Pubescence: | Slightly tomentose on upper surface, moderately tomentose on lower. More visible in dry/warm conditions. |
| Petiole color: | RHS 142C-142D (Green Group) |
| Petiole and mid rib texture: | Furrowed on upper side with lower side deeply ribbed with ridges running parallel to the lengthwise orientation. Sparsely arachnoid. |
| 1. Basal rosette leaves | |
| Shape: | Deeply pinnatifid with sparsely ciliate margins, narrowly trullate overall. Narrowly acuminate apex. |
| Size: | Very large, >172.72 × 45.72 cm (68 × 18 inches) |
| Distance between leaf division: | 6.35-11.43 cm (2½- 4½ inches) |
| Division indentation length: | 16.51-41.275 cm (6½-16¼ inches) |
| Petiole length: | 30.48-48.26 cm (12-19 inches) |
| Petiole width: | 3.175-6.985 cm (1¼-2¾ inches) |
| Petiole thickness: | 0.635-1.905 cm (¼-¾inches) |
| Midrib thickness: | Thick |
| 2. Cauline leaves | |
| Shape: | Ensiform overall, uneven and sparse serrations with narrowly acuminate apex. Somewhat undulate and dente and sparsely ciliate at margins. |
| Number of leaves: | Approximately 73 |
| Size: | 17.78-60.96 cm (7-24 inches) |
| Stem (primary reproductive stem system) | |
| Length (ground level to base of terminal capitulum (bud)): | 106.68-127.0 cm (42-50 inches) |

TABLE 1-continued

| Plant Characteristics | |
|---|---|
| Circumference: (base of terminal capitulum (bud): | 7.62-12.065 cm (3-4.75 inches) |
| Circumference (base of stem): | Average: 24.13 cm (9½ inches) |
| Exterior texture: | Vertically ribbed, pubescent |
| Stem habit: | Upright, caulescent |
| Pubescence: | Sparsely arachnoid |
| Color: | RHS 142B-142C |
| Time of beginning of elongation: | Early to late |
| Involucre bracts | |
| Arrangement: | Imbricate |
| Quantity per Capitulum (average): | 52 outer - 35 inner |
| Outer bract | |
| Shape: | Predominately ovate with flattened base |
| Apex: | Retuse |
| Margin: | Entire |
| Base: | Slightly rounded |
| Texture: | Firm, thick and fleshy |
| Color: | RHS 141C-141D (Green Group) |
| Surface (outer/inner): | Glabrous |
| Spinosity: | Moderate frequency, woody |
| Length of spines: | 1-5 mm (0.04-0.2 inches) |
| Striation at base of lower bracts: | Present on approximately 20% of lower outside bracts. |
| Striation color: | RHS 77A (Purple-Violet Group) |
| Inner bract | |
| Shape: | Lanceolate with caudate tip |
| Apex: | Retuse |
| Margin: | Entire |
| Texture: | Firm, thinner than outer bract, fleshy |
| Base: | Slightly rounded |
| Color: | RHS 150B-150C (Green Group) |
| Surface (outer/inner): | Glabrous |
| Spinosity: | Finer than outer bract more frequent |
| Length of spines: | 1-2 mm (0.04-0.079 inches) |
| Capitulum (head/bud) - when ready for harvest as edible bud | |
| Color: | RHS 141C-141D (Green Group) |
| Shape: | Globose to ovoid |
| Apex: | Broadly rounded to obtuse |
| Base: | Truncate to rounded |
| Form: | Tightly compact |
| Texture: | Firm |
| Receptacle shape: | Concavo-convex |
| 1. Primary (Terminal) Capitulum | |
| Number per primary shoot | 1 |
| Circumference: | 32.385-38.1 cm (12¾-15 inches) |
| Weight: | Average 425 grams (0.94 lbs.) |
| Height: | Average 10.16 cm (4 inches) |
| Diameter: | 11.43-12.7 cm (4½-5 inches) |
| 2. Secondary capitulum | |
| Number per primary shoot | 3-5 |
| Circumference | 7.62-38.1 cm (3-15 inches) |
| Weight: | Average 237 grams (0.52 lbs.) |
| Height: | Average 8.255 cm (3¼inches) |
| Diameter: | 2.54-12.7 cm (1-5 inches) |

TABLE 1-continued

| Plant Characteristics | |
|---|---|
| 3. Tertiary capitulum | |
| Number per primary shoot | 2-5 |
| Circumference | 7.62-27.31 cm (3-10¾ inches) |
| Weight: | Average 44 grams (0.0970 lbs) |
| Height: | Average 6.78 cm (2⅔ inches) |
| Diameter: | 5.08-10.795 cm (2-4¼ inches) |
| Receptacle (heart) - when ready for harvest and edible | |
| Shape: | Concavo-convex |
| Circumference: | 8.89-25.4 cm (3½-10 inches) |
| Color: | RHS 150D (Green Group) |
| Texture: | Firm |
| Size: | Very thick and wide when compared to other globe varieties |
| Peduncle | |
| Shape: | Columnar |
| Length: | 2.54-76.2 cm (1-30 inches) |
| Diameter: | .635-3.81 cm (¼- 1½ inches) |
| Color: | RHS 142B-142C (Green Group) |
| Strength: | Strong and rigid |
| Surface: | Glabrous, slightly pubescent with shallow vertical ribbing |

COMPARISON WITH PARENTAL AND COMMERCIAL VARIETIES

When artichoke plant 'PAGA 15-1' is compared to the parental variety 'Green Globe' (unpatented), 'PAGA 15-1' produces larger sized secondary and tertiary buds and in greater numbers. Additionally, 'PAGA 15-1' exhibits less phenotypic variation when grown in the field.

When artichoke plant 'PAGA 15-1' is compared to the commercial variety 'PAGA G-1' (U.S. Plant patent application Ser. No. 16/501,358), 'PAGA 15-1' produces at least 12 lateral buds on the primary reproductive shoots and on average 4 secondary reproductive shoots during the first production cycle, and has frequent spinosity on outer bract; whereas 'PAGA G-1' produces at least 9 lateral buds on the primary reproductive shoots and on average 3 secondary reproductive shoots during the first production cycle, and has a moderate frequency of spinosity on outer bract.

When artichoke plant 'PAGA 15-1' is compared to the commercial variety 'PAGA 13-1' (U.S. Plant patent application Ser. No. 16/501,354), 'PAGA 15-1' produces at least 12 lateral buds on the primary reproductive shoots and on average 4 secondary reproductive shoots during the first production cycle, has an early maturity, and has a capitulum shape of globose to ovoid; whereas 'PAGA 13-1' produces at least 20 lateral buds on the primary reproductive shoots and on average 6 secondary reproductive shoots during the first production cycle, has a late maturity, and has a capitulum shape of sub-globose with slightly flattened base and top.

I claim:

1. A new and distinct variety of artichoke plant named 'PAGA 15-1' as shown and described herein.

* * * * *